United States Patent [19]

Navaratnam et al.

[11] Patent Number: 5,200,324
[45] Date of Patent: Apr. 6, 1993

[54] METHOD OF DIAGNOSING SENILE DEMENTIA OF THE ALZHEIMER TYPE

[75] Inventors: Dasakumar S. Navaratnam; John D. Priddle; Brendon I. McDonald; A. David Smith; Kim A. Jobst, all of Oxford, England

[73] Assignee: E. R. Squibb & Sons, Inc., Princeton, N.J.

[21] Appl. No.: 739,040

[22] Filed: Aug. 1, 1991

Related U.S. Application Data

[63] Continuation-in-part of Ser. No. 576,886, Sep. 4, 1990, abandoned.

[51] Int. Cl.$^5$ ............... C12Q 1/46; C12N 9/18; G01N 15/18
[52] U.S. Cl. ........................... 435/20; 435/197; 436/149
[58] Field of Search ............ 435/20, 197; 436/86, 436/149

[56] References Cited

PUBLICATIONS

Mesulam, M. M. et al, "Acetylcholinesterase-rich pyramidal neurons in the human neocortex and hippocampus: absence at birth, development during the life span, and dissolution in Alzheimer's disease," Ann. Neurol. 1988; 24:765-773.

Smith and Cuello, "Alzheimer's disease and acetylcholinesterase containing neurons," Lancet 1984; ii:513.

Chubb, I. W. et al, "Is acetylcholinesterase secreted from central neurons into cerebrospinal fluid?" Neuroscience 1976; 1:57-62.

Greenfield and Smith, "The influence of electrical stimulation of certain brain areas on the concentration of acetylcholinesterase in rabbit cerebrospinal fluid," Brain Res. 1979, 177:445-459.

Appleyard and Smith, "Spontaneous and carbachol--evoked in vivo secretion of acetylcholinesterase from the hippocampus of the rat," Neurochem. Int. 11, 397-406.

Johnson and Domino, "Cholinergic enzyme activity of cerebrospinal fluid of patients with various neurological disorders," Clin. Chem. Acta 1971, 35:421-428.

Davies, P., "Neurotransmitter-related enzymes in senile dementia of the Alzheimer type," Brain Res. 1979, 171:319-327.

Soininen et al, "Acetylcholinesterase activities in cerebrospinal fluid of patients with senile dementia of Alzheimer type," Acta Neurol. Scand. 1981, 64:217-224.

Appleyard et al, "Decrease CSF acetylcholinesterase activity in Alzheimer's disease," Lancet 1983, ii:452.

Appleyard et al, "Cholinesterase activities in cerebrospinal fluid of patients with senile dementia of the Alzheimer types," Brain 1987, 110:1309-1322.

Arendt et al, "Decreased ratio of CSF acetylcholinesterase to butyrylcholinesterase activity in Alzheimer's disease," Lancet 1984, i:173.

Primary Examiner—Johnnie R. Brown
Assistant Examiner—A. Varma
Attorney, Agent, or Firm—Burton Rodney

[57] ABSTRACT

A method is provided for the screening of senile dementia of the Alzheimer type (Alzheimer's disease) by testing for an anomalous molecular form of acetylcholinesterase in cerebrospinal fluid of a patient.

6 Claims, 2 Drawing Sheets

METHOD OF DIAGNOSING SENILE DEMENTIA OF THE ALZHEIMER TYPE

REFERENCE TO OTHER APPLICATIONS

This is a continuation-in-part of U.S. application Ser. No. 576,886, filed Sept. 4, 1990, now abandoned.

FIELD OF THE INVENTION

The present invention relates to a method of diagnosing for senile dementia of the Alzheimer type (SDAT or Alzheimer's disease) by testing for an anomalous form of acetylcholinesterase (AChE) in cerebrospinal fluid of a patient.

BACKGROUND OF THE INVENTION

One of the characteristic neurochemical changes in the brains of patients with Alzheimer's disease (AD) is a regional loss in the activity of enzyme markers of the cholinergic system (Perry E. K., "The cholinergic hypothesis—ten years on," Brit. Med. Bull. 1986; 42:63-69). One of these marker enzymes, acetylcholinesterase (AChE, E.C. 3.1.1.7), is, however, present in many of the non-cholinergic neurons in the cortex (Nakamura, S. et al, "Acetylcholinesterase and somatostatin-immunoreactivity coexist in human neocortex," Neurosci. Lett. 1985; 61:183-187; Mesulam, M. M. et al, "Acetylcholinesterase-rich pyramidal neurons in the human neocortex and hippocampus: absence at birth, development during the life span, and dissolution in Alzheimer's disease," Ann. Neurol. 1988; 24:765-773) and in subcortical nuclei (Smith and Cuello, "Alzheimer's disease and acetylcholinesterase-containing neurons," Lancet 1984; ii:513) that also show pathological changes in AD. Accordingly, it has been suggested that AD may be related to an abnormality in neurons that contain a particular molecular form of AChE, which could account for why many different transmitter systems are affected in the disease (Smith and Cuello, supra).

Certain molecular forms of AChE are secreted from nervous tissue into the cerebrospinal fluid (CSF) (Chubb, I. W. et al "Is acetylcholinesterase secreted from central neurons into cerebrospinal fluid?" Neuroscience 1976; 1:57-62; Greenfield and Smith, "The influence of electrical stimulation of certain brain areas on the concentration of acetylcholinesterase in rabbit cerebrospinal fluid," Brain Res. 1979, 177:445-459; and one of the brain regions most affected in AD, the hippocampus, has been shown to be a source of neurosecretory AChE (Appleyard & Smith, "Spontaneous and carbachol-evoked in vivo secretion of acetylcholinesterase from the hippocampus of the rat," Neurochem. Int. 11, 397-406). If the level of AChE in CSF reflects the levels of neuronal AChE in the brain, the widespread decrease in brain AChE levels in patients with AD might lead to lower than normal levels of AChE in the CSF. Since early reports (Johnson and Domino, "Cholinergic enzyme activity of cerebrospinal fluid of patients with various neurological disorders," Clin. Chem. Acta 1971, 35:421-428; Davies, P., "Neurotransmitter-related enzymes in senile dementia of the Alzheimer type," Brain Res. 1979, 171:319-327; Soininen et al, "Acetylcholinesterase activities in cerebrospinal fluid of patients with senile dementia of Alzheimer type," Acta neurol. scand. 1981, 64:217-224), there have been more than 20 accounts in the literature about cholinesterase activity in the CSF of patients with dementia, some of which have described lower levels than in non-demented patients, others of which have described no change in dementia. In the great majority of these reports, the diagnosis of AD was made only by clinical criteria. It is noteworthy that in those studies where histological criteria were used a significantly lower AChE level in ventricular CSF (Appleyard et al, "Decreased CSF acetylcholinesterase activity in Alzheimer's disease," Lancet 1983, ii:452; Appleyard et al, "Cholinesterase activities in cerebrospinal fluid of patients with senile dementia of the Alzheimer type," Brain 1987, 110:1309-1322) and in lumbar CSF (Arendt et al, "Decreased ratio of CSF acetylcholinesterase to butyrylcholinesterase activity in Alzheimer's disease," Lancet 1984, i:173) was found in patients with AD compared to controls. However, another study showed that the levels of AChE in the lumbar CSF of patients with histologically diagnosed AD overlapped with the levels in control patients and it was concluded that such measurements have no diagnostic value (Appleyard et al, 1987, supra).

DESCRIPTION OF THE INVENTION

It has been found that there are differences in the molecular forms of AChE in the CSF of patients with AD compared to patients without AD.

In accordance with the present invention, a method is provided of diagnosing or detecting presence of Alzheimer's disease (AD) which method is based upon the differences in the molecular forms of acetylcholinesterase (AChE) in the cerebrospinal fluid (CBF) of patients with histologically diagnosed Alzheimer's disease and normal age-matched controls.

The method of the present invention of diagnosing or detecting the presence of Alzheimer's disease includes the steps of determining the number and pattern of molecular forms of AChE in CSF of a patient, and determining if such number and pattern of molecular forms of AChE is greater than and different from that found in CSF in normal, preferably, age-matched controls. It has been found that patients with Alzheimer's disease will usually have at least one molecular form of AChE in CSF not present in normal age-matched controls.

Accordingly, where in carrying out the method of the present invention, it is determined that a patient has at least one molecular form of AChE in CSF not found in CSF of normal age-matched controls, a positive diagnosis of Alzheimer's disease may be made.

Where in carrying out the method of the present invention, it is determined that the number and pattern of molecular forms of AChE in CSF of a patient is the same as in normal age-matched controls, a negative diagnosis of Alzheimer's disease may be made.

The number and pattern of molecular forms of AChE in the CSF of both patients and controls may be determined by iso-electric focussing in polyacrylamide gels using a modification of the iso-electric focussing method of Giulian et al, "Analytical isoelectric focusing using a high-voltage vertical slab polyacrylamide gel system," Analyt. Biochem. 1984, 142:421-436.

The cholinesterase activity of the molecular forms of AChE in the gel may be determined by modification of a histochemical procedure for cholinesterase activity, as described by Chubb, I. W. and Smith A. D. (1975) "Isoenzymes of soluble and membrane-bound acetylcholinesterase in bovine splanchnic nerve and adrenal medulla," Proc. R.Soc.B 191, 245-261.

The test employed for determining levels of AChE activity in CSF of both patients and controls are as described by Ellman, G. L., Courtney, D. K., Andres, V. and Featherstone, R. M. (1961) "A new and rapid colorimetric determination of acetylcholinesterase activity," Biochem. Pharmacol. 7, 161-177, and Chubb and Smith supra.

The method of the invention may be carried out while the patient is alive or at post-mortem.

Thus, in accordance with the present invention, a patient having an extra molecular form of AChE in the particular isoelectric position demonstrated (for example, an extra molecular form over a particular pH range, namely from about 5 to about 7), which molecular form is not present in age-matched controls, will be diagnosed as having Alzheimer's disease.

It will be apparent to one skilled in the art that the presence of an extra molecular form of AChE in cerebrospinal fluid of a patient may be determined by means other than isoelectric focussing, such as by high-resolution methods of ion-exchange chromatography or any non-denaturing electrophoretic technique, like capillary electrophoresis.

The term "normal controls" or "normal aged-matched controls" refers to test subjects who do not have Alzheimer's disease.

EXAMPLE 1

Figure 1:
FIG. 1 is a polyacrylamide iso-electric focussing (pH range 5-7) of post-mortem cisternal CSF from two control patients, 2 samples from each.

The following experiment demonstrates the method of diagnosing for Alzheimer's disease carried out at post-mortem and which is reported by D. S. Navaratnam et al "Anomalous molecular form of acetylcholinesterase in cerebrospinal fluid in histologically diagnosed Alzheimer's disease," The Lancet, Vol. 337:447-450, Feb. 23, 1991.

PATIENTS AND METHODS

Nineteen patients with no reported dementia in life (10 males, 9 females; mean age 78.05±12, S.D.); 33 patients with a clinical diagnosis of definite, progressive dementia (12 males, 21 females; mean age 77.45±9) and 9 patients with possible dementia or confusion (5 males and 4 females; mean age 75±14) were studied. The diagnosis or causes of death in the non-demented group included chronic renal failure, schizophrenia, cerebrovascular accident, and Parkinson's disease.

Autopsies were performed on all patients in order to obtain samples of CSF and of brain tissue. The interval between death and postmortem in most cases was less than 65 hours: the mean interval for the non-demented group was 57 hours and for the demented group was 54.4 hours, and for the possibly demented group was 55 hours.

CSF was obtained as follows Cisternal CSF was obtained by aspirating the CSF in the subtentorial space with the exposed brain in situ; ventricular CSF by aspiration of the exposed ventricular cavities following bisection of the brain in the midline sagittal plane; and lumbar CSF by withdrawing fluid with a needle through the dura after dissection of the lumbar vertebral bodies. Samples of CSF were centrifuged at 3,000 g. for 30 minutes at 4° C.; the supernatant was then frozen at −70° C.. for storage. Prior to biochemical analysis the CSF was thawed, centrifuged at 50,000 g. for 2 hours (h) at 4° C., then divided into small volumes that were stored frozen at −20° C..

Neuropathological examination was carried out on cerebral hemispheres after they had been fixed in neutral formalin for at least four weeks. Histological sections from frontal, temporal, and parietal neocortex (Brodmann areas 9, 21/22 and 7, respectively), hippocampus, parahippocampal gyrus, midbrain and pons were stained with methenamine silver to show plaques (Lamy et al, "Comparison of seven staining methods for senile plaques and neurofibrillary tangles in a prospective series of 15 elderly patients," Neuropath. Appl. Neurobiol. 1989, 15:563-578), a modification (Cross, R. B., "Demontration of neurofibrillary tangles in paraffin section—a quick and simple method using Palmgren's technique," Med. Lab. Sci. 1982, 39:67-69) of the palmgren stain to show neurofibrillary tangles, luxol fast blue cresyl violet, haematoxylin and eosin, and congo red. The numbers of plaques were counted at ×100 magnification in a representative 1 sq. mm area of each cortical lobe examined. A semiquantitative estimate of the frequency of neurofibrillary tangles in hippocampus and cortex, of granulovacuolar degeneration and Hirano bodies in the hippocampus, and of vascular amyloid in leptomeningeal and cortical blood vessels was also recorded. A pathological diagnosis of AD was made if the criteria proposed by Khachaturian, "Diagnosis of Alzheimer's disease," Arch. Neurol. 1985, 42:1097-1105, were fulfilled, no account being taken of the clinical history. Other pathology discovered upon examination of the brain was also recorded.

Demonstration of molecular forms of AChE was done by iso-electric focussing in polyacrylamide gels. A modification of the iso-electric focussing method of Giulian et al, supra, was applied using a Hoefer SE 250 vertical apparatus. The gel was made by degassing a solution comprising 3.8 ml deionised water, 1.1 ml. acrylamide monomers solution (5.84 g. acrylamide plus 0.16 g. bis-acrylamide made up to 20 ml), 0.42 ml ampholine pH 5-7 (LKB Ltd.) and 0.6 ml glycerol; this solution was then polymerized by addition of 11.5 $\mu$l N,N,N',N'-tetramethyl ethylenediamine (TEMED) and 12.5 $\mu$l 10% ammonium persulphate and cast into a frame containing a GelBond PAG support film (FMC Co.). After one hour, the gel was pre-focussed at 200V for 10 minutes, 300V for 10 minutes and then for one hour at 400V at constant voltage. The catholyte and anolyte were, respectively, extensively degassed solutions of 20 mM L-histidine and DL-glutamic acid. The AChE activity of CSF was determined at 30° C. (Ellman et al, supra), using the specific inhibitor 1,5-bis-(4-allyldimethylammonium-phenyl)pentan-3-one dibromide (BW 284 C51) ($1.5 \times 10^{-6}$M, Sigma Chemicals), and a volume of CSF containing 1.2 nmole/min of activity was concentrated to approximately 50 $\mu$l by centrifugation through a low protein binding 10,000 nominal molecular weight limit ultrafilter (Ultrafree-MC, Millipore). The sample was then mixed with 200 $\mu$l 6% ampholine containing 0.1% Tween 20 and the mixture was further concentrated to a final volume of approximately 20 $\mu$l. The sample was loaded at the cathodic end (top) of the vertical gel, and then allowed to enter the gel at 300V. The gel was focussed at 1000V (constant voltage) for 3.5 hours with continuous water cooling. Bovine erythrocyte carbonic anhydrase and β-lactoglobulin served as markers. The molecular forms of AChE in the gel were revealed by a modification (Chubb and Smith, supra) of the histochemical procedure for cholinesterase activity with acetylthiocholine as substrate. Gels were incubated with the substrate for 17-20 h at 30° in order to develop the bands. In experiments in which it was necessary to distinguish AChE from non-specific cholinesterase, the specific inhibitor of AChE (BW 284 C51, $1.5 \times 10^{-6}$ M, Sigma Chemicals) was added to the incubation mixture.

Results

Figure 2:
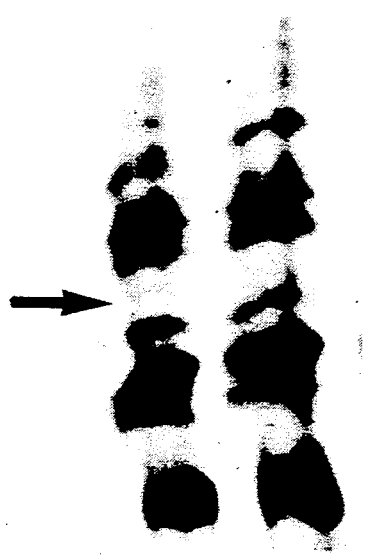
FIG. 2 is a polyacrylamide iso-electric focussing (pH range 5-7) of post-mortem cisternal CSF. (A) CSF from patient with Alzheimer's disease; (B) CSF from control. Arrow points to anomalous band.

The samples of CSF were all analysed by isoelectric focussing without prior knowledge of the diagnosis. The samples came from 19 patients without clinical signs of dementia, from 9 patients with possible dementia or confusion, and from 33 patients with definite, progressive dementia. The bulk of the AChE activity in CSF was recovered as a series of bands that equilibrated between pH 5 and pH 7; the location of the eight more strongly staining bands was consistent between patients and between samples of CSF from the same patient irrespective of whether it was obtained from the ventricles, cisternal magna or spinal cord (FIG. 1). In 21 of the definitely demented patients one or more sample of CSF contained an additional band that focussed inbetween two of the strongly-reactive bands in normal CSF (FIG. 2). The cholinesterase activity of this band was inhibited when the gel was incubated in the presence of the specific inhibitor of AChE (BW 284 C51) and so the band was due to AChE activity. The anomalous form of AChE occurred in the CSF of 21 out of 31 demented patients who fulfilled the criteria of Khachaturian, supra, for a histological diagnosis of AD (Table 1). In particular, the anomalous band was present in 19 out of the 23 patients who had a histological diagnosis of AD but no other obvious CNS pathology (Table 1). The anomalous band is labelled 'AChE-AD'.

In the group of 9 patients that possibly had dementia the anomalous band was present in 4 samples of CSF; three of these came from patients with plaque and tangle counts that did not reach the criteria of Khachaturian, supra, for a diagnosis of AD, but which are assumed to indicate age-related changes (Table 1).

The distribution of AChE-AD in the CSF in the patients with a histological diagnosis of AD is shown in more detail in Table 2. As can be seen, AChE-AD was most frequently found in cisternal CSF. Apart from two cases (one where AChE-AD was present in ventricular CSF and one where it was in lumbar CSF), all cases where AChE-AD was found in either lumbar or ventricular CSF also displayed the band in cisternal CSF.

The anomalous form (AChE-AD) of acetylcholinesterase was not detected in any of the CSF samples from the 19 non-demented patients: altogether 49 samples were analysed, of which 17 were ventricular, 19 were cisternal, and 13 were lumbar CSF.

The finding of an anomalous molecular form of AChE in the CSF of the majority (67%) of patients with progressive dementia and histologically diagnosed AD is consistent with the hypothesis described hereinbefore, that the disease is associated with neurons that contain AChE. The result raises the possibility that some aspect of the neuronal synthesis storage and/or secretion of AChE is unusual in this disease. Since AChE-AD was most consistently found in cisternal CSF, it is possible that the abnormality occurs mainly in neurons in the brain stem, many of which show neurofibrillary tangles in AD. It is noteworthy that previous studies have indicated that certain kinetic properties of AChE in the brain (Perry et al, "Changes in brain cholinesterases in senile dementia of the Alzheimer type," Neuropath. Appl. Neurobiol. 1978, 4:273-277; Geula et al, "Special properties of cholinesterases in the cerebral cortex of Alzheimer's disease," Brain Res. 1989, 498:185-189) and CSF (Appleyard 1987, supra) of patients with AD are different from normal, which also suggests some change in AChE at the molecular level.

It should be pointed out that AChE-AD was present in the CSF of four out of nine possibly demented patients who did not fulfill the strict histological criteria for AD.

As basis of employing the above finding as an antemortem test, AChE-AD could not be detected in the CSF from any of the non-demented patients, whereas it was present in 82% of patients with a 'pure' diagnosis of AD.

TABLE 1

Occurrence of an anomalous molecular form of AChE in CSF of patients with, or without, dementia.

| Histopathological diagnosis | AChE-AD present |
|---|---|
| Definite progressive dementia (n = 33) | |
| 'Pure' Alzheimer's disease (n = 23) | 19 |
| AD plus other pathology# (n = 8) | 2 |
| Pick's disease (n = 1) | 0 |
| Multi-infarct dementia (n = 1) | 0 |
| Possible dementia or confusion (n = 9) | |
| Age-related change* (n = 4) | 2 |
| Age-related* and ischaemia (n = 2) | 1 |
| Ischaemia only (n = 1) | 1 |
| Paraneoplastic (n = 1) | 0 |
| No neuropathology (n = 1) | 0 |
| No identified dementia or confusion (n = 19) | |
| Age-related change* (n = 12) | 0 |
| Mild AD pathology (n = 1) | 0 |
| Ischaemic lesion (n = 2) | 0 |
| Parkinson's disease (n = 1) | 0 |
| Hydrocephalous** (n = 1) | 0 |
| No neuropathology (n = 2) | 0 |

AChE-AD refers to the anomalous band of AChE activity found after isoelectric focussing.
AD plus Parkinson's disease (n = 4); AD plus ischaemic lesion(s) (n = 3); AD plus meningioma (n = 1).
*Few plaques and tangles, insufficient to meet Khachaturian criteria for diagnosis of AD.
**Had a clinical diagnosis of schizophrenia.
Abbreviation: AD, Alzheimer's disease defined according to the histopathological criteria of Khachaturian, supra (1985).

TABLE 2

Distribution of anomalous AChE molecular form between CSF obtained from different sites in patients with histopathologically-demonstrated Alzheimer's disease

| | Ventricular CSF | Cisternal CSF | Lumbar CSF |
|---|---|---|---|
| 'Pure' AD | 1/21 | 17/23 | 9/21 |
| AD plus other | 0/8 | 2/8 | 2/6 |

The figures show the number of samples containing the extra band (AChE-AD) out of the total available for analysis. One group of patients had AD without any other obvious CNS pathology ('pure' AD); another group had AD together with other CNS pathology (see Table 1).
Abbreviation: AD, Alzheimer's disease defined according to the histopathological criteria of Khachaturian, supra.

SUMMARY

Cerebrospinal fluid obtained post-mortem contains several molecular forms of acetylcholinesterase (AChE) that can be revealed by iso-electric focussing. The cerebrospinal fluid from 19 out of 23 patients with both clinical dementia and a histological diagnosis of Alzheimer's disease uncomplicated by other CNS disease contained an additional molecular form of AChE which could not be detected in the cerebrospinal fluid from 19 age-matched patients with no clinical dementia or pathological signs of Alzheimer's disease. The cerebrospinal fluid of 2 out of 8 demented patients who had pathological signs of other CNS disease, such as Parkinson's disease, as well as histological evidence of Alzheimer's disease also contained the anomalous form of AChE. The anomalous band was present in the CSF of 4 out of 8 patients with a clinical diagnosis of possible dementia, but who did not satisfy strict histopathological criteria for Alzheimer's disease.

The absence of the anomalous form of AChE in the CSF of non-demented patients and its presence in the CSF of the majority of patients with Alzheimer's disease forms the basis of an antemortem diagnostic test.

EXAMPLE 2

The following experiment demonstrates the method of diagnosing for Alzheimer's disease by determining the presence of an anomalous molecular form of acetylcholinesterase in lumbar CSF, carried out during life.

PATIENTS AND METHODS

Iso-electric focussing was used to reveal the molecular forms of acetylcholinesterase (AChE) in lumbar cerebrospinal fluid (CSF) obtained in life in a prospective study that includes more than 150 patients referred with memory problems. In this manner, it could be determined whether the same anomalous molecular form of AChE as that described earlier in CSF obtained at necropsy from patients with Alzheimer's disease (as shown in Example 1) could be detected in lumbar CSF obtained by lumbar puncture during life.

The following are interim findings on the first 15 patients in the study where a histopathological diagnosis of Alzheimer's disease has been made.

The anomalous molecular form of AChE (AChE-AD) could be revealed in lumbar CSF taken in life from patients who were clinically demented, who subsequently came to necropsy and were found to have a histopathological diagnosis (Khachaturian, supra) of Alzheimer's disease (Table 3). It should be noted that the patient with progressive supranuclear palsy was demented in life and had a high density of neurofibrillary tangles in the cerebral cortex.

Detection of AChE-AD in lumbar CSF depends upon the amount of CSF analyzed. In Example 1, an amount of CSF was applied to the gel that contained 1.25 nmol/min activity at 30 deg. C of AChE. It has been found that AChE-AD is more often detected in CSF if a larger amount of AChE activity is applied to the gel (Table 3). Accordingly, CSF containing 5 nmol/min of AChE activity was analyzed.

TABLE 3

Detection of anomalous form of acetylcholinesterase (AChE-AD) in lumbar-cerebrospinal fluid

| Histopathological diagnosis | Number of patients with AChE-AD in lumbar CSF/ number tested AChE activity applied to gel (nmol/min) | | |
|---|---|---|---|
| | 1.25 | 2.5 | 5.0 |
| Alzheimer's disease (n = 8) | 6/8 | 8/8 | 8/8 |
| Alzheimer's disease plus other pathology (n = 6) | 2/6 | 3/6 | 6/6 |
| Normal pressure hydrocephalus (n = 1) | 0/1 | 0/1 | 0/1 |

As can be seen from Table 3, included in this sensitivity study were those patients in the study who had died so that the findings on CSF in life with the histopathological diagnosis could be compared. There was a remarkable agreement between the presence of the anomalous form of AChE in CSF in life and the histological diagnosis of Alzheimer's disease. Because, so far, only one of the patients who had died did not have Alzheimer's disease, "controls" from Example 1 (Navaratnam et al, supra) were employed. Samples of CSF from patients with no signs of dementia in life who did not fulfill histopathological criteria for a diagnosis of Alzheimer's disease were studied at loadings of 5 (n=11 patients), 10 (n=10) and 20 mU (n=3) of AChE activity per gel track. In no case could the anomalous band be detected. Thus, no "false-positive" results were obtained in this group of "control" patients even when large amounts of CSF were applied to the gel. Therefore, a loading of 5 mU per track was adopted as the standard procedure for screening CSF for the presence of the anomalous form of AChE.

A second technical problem concerns the interpretation of the iso-electric focussing gels. The anomalous band was often rather faint and the gel runs are not always ideal. Accordingly, a procedure was adopted whereby 4 individuals independently "read" the gels and recorded their interpretations. For the first 63 samples, there was complete consensus on 45 samples. In most of the other samples, the technical quality of the gel run was the factor making interpretation difficult; these samples are being re-run. The results from the above 45 CSF samples, as yet not decoded for clinical diagnosis, show the following: 30 contained the anomalous form of the AChE and 15 did not.

What is claimed is:

1. A method of screening for Alzheimer's disease, which comprises determining by means of iso-electric focussing, if a patient has an anomalous molecular form of acetylcholinesterase (AChE) in his cerebrospinal fluid, which anomalous molecular form is not found in cerebrospinal fluid in a normal age-matched control, the presence of said anomalous molecular form of AChE in the patient indicative of the presence of Alzheimer's disease.

2. The method as defined in claim 1 wherein the presence of the anomalous molecular form of AchE is present at a pH range of from about 5 to about 7.

3. A method of screening for Alzheimer's disease, which comprises determining the number and pattern of molecular forms of acetylcholinesterase (AChE) in the cerebrospinal fluid of a patient, by means of iso-electric focussing, and when the number and pattern of molecular forms of acetylcholinesterase includes an anomalous molecular form not found in cerebrospinal fluid in normal age-matched controls, the presence of said anomalous molecular form of AChE not found in the normal age-matched controls is indicative of the presence of Alzheimer's disease.

4. The method as defined in claim 2 carried out ante-mortem.

5. The method as defined in claim 2 carried out post-mortem.

6. The method as defined in claim 2 wherein the molecular forms of AChE in cerebrospinal fluid of a patient is determined by iso-electric focussing at a pH of from about 5 to about 7.

* * * * *